(12) United States Patent
Lin et al.

(10) Patent No.: US 7,063,862 B2
(45) Date of Patent: Jun. 20, 2006

(54) PHARMACEUTICAL COMPOSITION AND METHOD FOR TREATING

(75) Inventors: Jenny Li-Ying Lin, San Jose, CA (US); David Wong, Milpitas, CA (US); San-Laung Chow, San Jose, CA (US)

(73) Assignee: BioKey, Inc., Fremont, CA (US)

( * ) Notice: Subject to any disclaimer, the term of this patent is extended or adjusted under 35 U.S.C. 154(b) by 0 days.

(21) Appl. No.: 10/454,240

(22) Filed: Jun. 3, 2003

(65) Prior Publication Data

US 2004/0247679 A1    Dec. 9, 2004

(51) Int. Cl.
*A61K 9/20*    (2006.01)
*A61K 31/70*    (2006.01)

(52) U.S. Cl. ............... 424/465; 424/468; 424/480; 514/29

(58) Field of Classification Search ............... 514/29; 424/468, 480, 481, 488, 465
See application file for complete search history.

(56) References Cited

U.S. PATENT DOCUMENTS

| | | | |
|---|---|---|---|
| 4,369,172 A | 1/1983 | Schor et al. ............... 424/19 |
| 4,681,755 A | 7/1987 | Colombo et al. | |
| 4,808,411 A | 2/1989 | Lu et al. ............... 424/441 |
| 4,842,866 A | 6/1989 | Horder et al. ............... 424/468 |
| 5,393,765 A | 2/1995 | Infeld et al. ............... 514/365 |
| 5,695,781 A * | 12/1997 | Zhang et al. ............... 424/468 |
| 5,705,190 A | 1/1998 | Broad et al. ............... 424/465 |
| 6,010,718 A | 1/2000 | Al-Razzak et al. ............... 424/464 |
| 6,673,369 B1 * | 1/2004 | Rampal et al. ............... 424/468 |
| 2002/0081332 A1 | 6/2002 | Rampal et al. | |

FOREIGN PATENT DOCUMENTS

| | | |
|---|---|---|
| EP | 293885 | 1/1988 |
| EP | 0 947 196 A1 | 10/1999 |
| WO | WO 95/30422 | 11/1995 |
| WO | WO 97/22335 | 6/1997 |
| WO | WO 03/063438 A1 | 7/2003 |

OTHER PUBLICATIONS

Rao et al., "Influence of Molecular Size and Water Solubility of the Solute on its Release from Swelling and Erosion Controlled Polymeric Matrices," *Journal of Controlled Release*, 12 (1990) 133-141.
PCT International Search Report from International Application No. PCT/US 2004/015953, dated Nov. 30, 2004.

* cited by examiner

*Primary Examiner*—Elli Peselev
(74) *Attorney, Agent, or Firm*—Ya-Fen Chen; Patterson & Sheridan LLP

(57) ABSTRACT

Embodiments of the invention generally provide pharmaceutical drug compositions, methods of preparing oral drug compositions, such as extended release dosage compositions, and methods for treating infection. More particularly, the invention relates to formulations containing a drug and a carrier material. In one aspect, the invention provides a pharmaceutical formulation including a therapeutically active agent, from about 0.1% to about 4.9% by weight of a pharmaceutically acceptable polymer, and from about 0.1% to about 30% by weight of a pharmaceutically acceptable acid, wherein the pharmaceutical composition have a zero order release profile of the therapeutically active agent. In another aspect, the invention provides methods for preparing and administering a pharmaceutical antibiotic composition in oral dosage form, such as a tablet.

30 Claims, 1 Drawing Sheet

PHARMACEUTICAL COMPOSITION AND METHOD FOR TREATING

BACKGROUND OF THE INVENTION

The invention generally relates to pharmaceutical compositions, such as drug formulations present in a solid form for oral administration. More particularly, the invention relates to long-lasting sustained dosage compositions, and carriers and active ingredients in the compositions thereof, such as extended release drug compositions for oral controlled release dosage formulations containing a drug and a carrier material.

Drug delivery at a predetermined rate such that drug concentrations can be maintained at therapeutically effective levels over an extended period, has received a great deal of attention. Many known solid drug formulations are required to be taken orally three times a day. There is a need for oral formulations to be taken less often, such as once per day.

Various approaches exist for preparing sustained or controlled release pharmaceutical formulations, such as various extended release formulations in tablet or capsule form. For example, one method of forming delayed or sustained release formulations includes coating the tablet with a release-retarding coating, or coating individual granules with such a coating, and compressing these coated granules into a tablet. One exemplary technique involves controlled release solid preparations for erythromycin derivatives in an alginate matrix, such as a matrix having a water-soluble alginate and a complex salt of alginic acid as described in U.S. Pat. No. 4,842,866, issued Jun. 27, 1989.

Another example involves controlled release tablet formulation for clarithromycin by using a matrix or carrier at high concentration of 5% to 50% of hydroxypropyl methylcellulose, such as 10%, 20% or 30% of hydroxypropyl methylcellulose, to be mixed or dispersed throughout the tablet, as described in U.S. Pat. No. 6,010,718, issued on Jan. 4, 2000.

However, in the preparation of delayed or sustained release forms of drug active ingredients, high concentration of soluble polymers often result in extremely slow drug dissolution, poor or variable drug release, poor or variable absorption, and acid instability at variable pH environments throughout the whole gastrointestinal (GI) tract. This is especially significant for relatively insoluble drug active ingredients, such as some poorly soluble antibiotics, e.g., macrolide antibiotics, which have been used extensively in treating a wide range of bacterial infections. Particularly, such problems occur when formulating erythromycin and its derivatives, such as 6-O-methylerythromycin A (clarithromycin), useful in treating common infections of the middle ear and upper respiratory tract.

Therefore, there is a need for an improved controlled release formulation and method for preparing such a controlled release formulation, and for a method of treating infection.

SUMMARY OF THE INVENTION

The invention generally provides a pharmaceutical composition having a therapeutically active agent, from about 0.1% to about 4.9% by weight of a pharmaceutically acceptable polymer, and from about 0.1% to about 30% by weight of a pharmaceutically acceptable acid, wherein the pharmaceutical composition has a zero order release profile of the therapeutically active agent.

In one aspect, an extended release pharmaceutical composition having a core of a pharmaceutical mixture, and a coating layer of a pharmaceutically acceptable coating material is provided. The pharmaceutical mixture generally includes a therapeutically active agent, from about 0.1% to about 4.9% by weight of a pharmaceutically acceptable polymer, and from about 0.1% to about 30% by weight of a pharmaceutically acceptable acid, such that the release profile of the therapeutically active agent is at a zero order rate.

For example, a pharmaceutical mixture having from about 10% to about 90% of an antibiotic, from about 0.1% to about 4.9% by weight of a pharmaceutically acceptable polymer, and from about 0.1% to about 30% by weight of a pharmaceutically acceptable acid is incorporated into a tablet core and coated with a coating layer of a pharmaceutically acceptable coating material, such that the release profile of the antibiotic is at a zero order rate.

In another aspect, the invention further provides a method of preparing a pharmaceutical composition. The method includes forming a core having a pharmaceutical mixture and coating the core with a coating layer of a pharmaceutically acceptable coating material. The pharmaceutical mixture includes a therapeutically active agent, from about 0.1% to about 4.9% by weight of a pharmaceutically acceptable polymer, and from about 0.1% to about 30% by weight of a pharmaceutically acceptable acid.

In addition, a method of administering an extended release pharmaceutical composition is provided. The method includes administering a pharmaceutical composition in an effective amount to a mammal for the treatment of bacterial infection.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
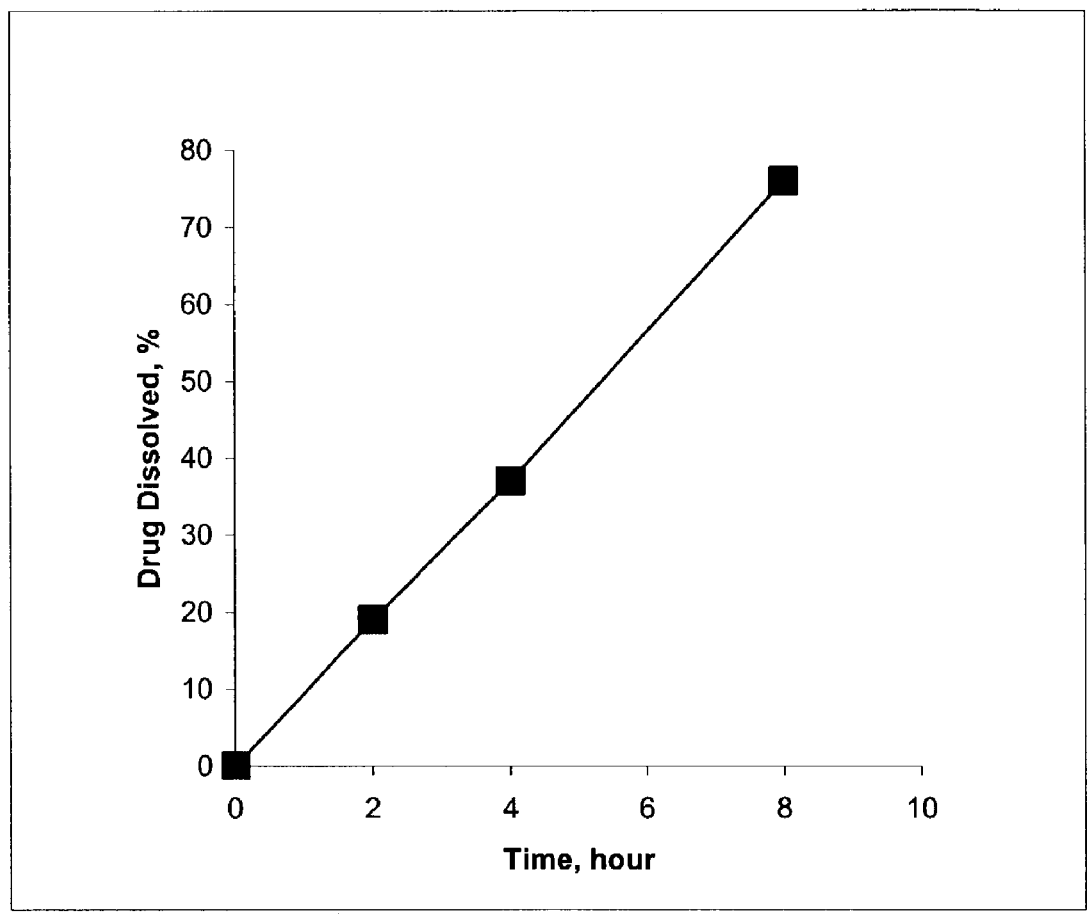
FIG. 1 is a release profile of an exemplary pharmaceutical composition.

The pharmaceutical composition of the invention includes a therapeutically active agent, a pharmaceutically acceptable polymer, and a pharmaceutically acceptable acid. The pharmaceutical composition is generally prepared into an oral dosage form or a solid dosage form, such as a tablet, a capsule, a sachet etc., and any therapeutically acceptable form.

The therapeutically active agent is generally an active ingredient compound having a therapeutic effect and including anti-hypertensives, calcium channel blockers, β-blockers, analgesics, anti-neoplastic agents, anti-microbials, anti-malarials, non-steroidal anti-inflammatory drugs (NSAID), diuretics, anti-arrythmia agents and the like. Preferably, the therapeutically active agent exhibits a therapeutic effect in treating infections by a microbial agent. Examples of such therapeutically active agent include antibiotics, anti-infection agents, and anti-microbial agents, including, but not limited to macrolide antibiotic, β-lactam antibiotic, amoxicillin, rifampicin, tetracycline, penicillin, and others. One example is erythromycin and/or its derivatives, such as azithromycin. Another example is an erythromycin derivative, 6-O-methoxy erythromycin A, also known as clarithromycin. Other examples include nifedipine, nisoldipine, nicardipine, nilvadipine, felodipine, bendroflumethazide, acetazolamide, methazolamide, chlorpropamide, methotrexate, allopurinol, hydrocortisone, triamcinolone, prednisone, prednisolone, norgestrel, norethindone, progesterone, norgesterone, ibuprofen, atenolol, timolol, cimetidine, clonidine, diclofenac and the like.

The amount of the therapeutically active agent may be utilized at therapeutic dose levels and varies from about 10% to about 95% by weight of the pharmaceutical composition, preferably, from about 30% to about 80% by weight of the pharmaceutical composition. One example, of the pharmaceutical composition includes clarithromycin of about 45% to about 55% by weight.

The therapeutically active agent can be prepared into powder, granules, particles, beads, pellets, and other pharmaceutical acceptable sizes. The therapeutically active agent can further be micronized and preferably have a particle size of less than 20 microns.

The pharmaceutically acceptable polymer includes, but is not limited to, water-soluble hydrophilic polymers, maltodextrin, natural gums, arabic gum, guar gum, xanthan gum, tragacanth gum, agar, gellan gum, kayara gum, alginic acids, pectins, pre-gelatinized starch, dextrin, maltodextrin, and blends of these polymers, and combinations thereof. Examples of water-soluble polymers include polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and mixtures thereof.

Particularly useful water-soluble hydrophilic polymer blends are those which can interact with water and aqueous biological fluids and then swell or expand to an equilibrium state, such as those that swell under the environment of the gastrointestinal tract to retain a significant portion of the imbibed or absorbed fluid for delaying the release of the therapeutically active agent. Other useful water-soluble hydrophilic polymers can form association polymers in the low pH environment of the stomach.

The high molecular weight water-soluble polymers, such as hydroxypropyl methylcellulose (HPMC) can have an average molecular weight greater than 50,000, such as greater than 100,000 and greater than 200,000. For example, polyvinylpyrrolidone can have an average molecular weight from about 10,000 to about 250,000, such as greater than 100,000, and greater than 120,000.

Preferably, the pharmaceutically acceptable polymer is selected from hydroxypropyl cellulose, hydroxypropyl methylcellulose, and methylcellulose. More preferably, the pharmaceutically acceptable polymers are hydroxypropyl methylcellulose and polyvinylpyrrolidone. Most preferably, the hydroxypropyl methylcellulose is a high viscosity hydroxypropyl methylcellulose of U.S.P. substitution type 2208 with viscosity of about 5,000 centipoises (cps) or greater. Centipoise is equivalent to mPa·s (millipascal-second) and all solution viscosities are measured at 2% concentration in water at 20° C. (68° F.). The methyoxy content of the hydroxypropyl methylcellulose can be approximately from about 19% to about 24% by weight and the hydroxypropyl content of the hydroxypropyl methylcellulose can be approximately from about 7% to about 8.5% by weight. As an example, one suitable grade of hydroxypropyl methylcellulose is available from Dow Chemical Co. of Midland, Mich. under the tradename METHOCEL K100M which exhibits a viscosity in a 2% aqueous solution of approximately 100,000 cps.

As another example, the pharmaceutically acceptable polymer is polyvinylpyrrolidone of a high viscosity with viscosity of 55 cps or greater. Polyvinylpyrrolidone (PVP) is a linear homopolymer or copolymer having at least about 80%, preferably at least about 90% of repeat units derived from 1-vinyl-2-pyrrolidone monomers. The PVP polymer more preferably contains at least about 95% or essentially all of such repeat units and the remainder portion can be any of the various polymerization-compatible monomers, e.g., neutral monomers, such as alkenes or acrylates. Other synonyms for PVP include povidone, polyvidone, 1-vinyl-2-pyrolidinone, and 1-ethenyl-2-pyrolionone (CAS registry number 9003-39-8). PVP polymers materials are sold by various companies, including ISP Technologies, Inc. under the trademark PLASDONE™ K-29/32; BASF Aktiengesellschaf under the trademark KOLLIDON™ for USP grade PVP, for example KOLLIDON™ K-30 or K-90 (BASF Corporation, NV Division, 3000 Continental, Mount Olive, N.J. 07628-1234, USA). It is to be understood, however, that the invention is not limited to any specific PVP and that any equivalent PVP of acceptable purity, preferably pharmaceutical grade, may be used. For example, povidone can be suitably present in a total amount of from about 0.2% to about 4.9% by weight, such as from about 0.2% to about 2% by weight of the pharmaceutical composition.

The amount of the pharmaceutically acceptable polymer in the pharmaceutical composition generally varies from about 0.1% to about 4.9% by weight of the pharmaceutical composition, such as from about 1.5% to about 4.5% by weight of the pharmaceutical composition. Preferably, the amount of pharmaceutically acceptable polymer varies from about 2.5% to about 4% by weight.

The pharmaceutical composition of the invention also includes a pharmaceutically acceptable acid including, but not limited to, various organic acids, carboxylic acids, keto acids, α-hydroxy acids, β-hydroxy acids, and derivatives and combinations thereof. For example, tartaric acid, fumaric acid, malic acid, citric acid, succinic acid, glutaric acid, glutamic acid, maleic acid, or mandelic acid, can be used herein. One suitable pharmaceutically acceptable acid is citric acid.

The amount of the pharmaceutically acceptable acid in the pharmaceutical composition generally varies from about 0.1% to about 30% by weight of the pharmaceutical composition, such as from about 0.1% to about 10% by weight of the pharmaceutical composition. Not wishing to be bound by any theory, it is believed that the pharmaceutically acceptable acid in the pharmaceutical composition enhances the gelling process of the pharmaceutical acceptable polymer to achieve the zero-order drug release profile.

In one embodiment, the invention provides extended release formulations for the therapeutically active agent. For example, the pharmaceutical composition of the invention includes a controlled release, sustained release, or timed release dosage formulation for the therapeutically active agent, such as an antibiotic. The extended release formulation as described herein can provide continuous and non-pulsating therapeutic levels of the therapeutically active agent to a mammal in need of such treatment over a period of time, such as a six-hour period or longer, e.g., a twelve-hour to twenty-four hour period. Such an extended release, controlled release, sustained release, or timed release dosage formulation employs a mixture of an organic acid and water-soluble polymers, e.g., a high molecular weight hydroxypropyl methylcellulose and polyvinylpyrrolidone, to provide a zero order release profile of an antibiotic.

In one aspect, the dosage forms of the pharmaceutical composition prepared according to the invention exhibit a zero order release profile. The term "zero order" is broadly defined herein as the release of a compound proportional to time, regardless of the concentration or the strength of the compound. The term "release" is broadly defined herein as absorption or dissolution of a compound, either in vivo or in vitro. The in vivo absorption is generally performed by measuring the plasma concentration of the therapeutically active agent over a period of time. The in vitro release profile of the therapeutically active agent can be tested in a USP type 2 apparatus at about 50 rpm in about 900 ml of phosphate buffer (pH 5) and at 37° C. Other standard USP testing conditions can also be used. For example, acetate buffer (pH 5) can be used herein.

In another aspect, the pharmaceutical composition of the invention provides up to about 30% release of the therapeutically active agent during the initial 2 hours, preferably from about 5% to about 30% release. The pharmaceutical composition further provides from about 30% to about 90% release of the therapeutically active agent within 6 hours, preferably from about 30% to about 80% release. Within 12 hours, the pharmaceutical composition provides not less than about 50% release of the therapeutically active agent, preferably not less than about 75% release.

In another embodiment, the invention provides extended release formulations having a core of a pharmaceutical mixture, and a coating layer of a pharmaceutically acceptable coating material. The pharmaceutical mixture generally includes a therapeutically active agent, from about 0.1% to about 4.9% by weight of a pharmaceutically acceptable polymer, and from about 0.1% to about 30% by weight of a pharmaceutically acceptable acid, such that the release profile of the therapeutically active agent is at a zero order release rate.

The pharmaceutical mixture may further include pharmaceutically acceptable excipients, fillers, binders and blending agents, such as hydrous or anhydrous form of lactose, starches, glucose, sucrose, mannitol, sorbitol, silicic acid, microcrystalline celluloses, sodium carboxymethylcelluloses, sodium starch glycolate, and derivatives and mixtures thereof. For example, anhydrous lactose can be added into the pharmaceutical mixture to a concentration of from about 1% to about 80% by weight of the pharmaceutical composition, such as from about 5% to about 40% by weight.

The pharmaceutical mixture can further include surfactants, emulsifiers, dispersing agents, defoamers, and mixtures thereof. Any of the pharmaceutically acceptable or medicinally acceptable surfactants, emulsifiers, dispersing agents, dispersants, and defoamers can be used herein. For example, Tween 80 (available form Fisher Scientific International), Tween 20, Tween 100, sodium lauryl sulfate, and others can be used to a concentration of no more than 50%, such as from about 0.1% to about 10%. The pharmaceutical composition of the invention may further include lubricants, blenders, anti-sticking agents, glidants, wetting agents, dyes, pigments, nonstick agents, dispersants, blenders, coating materials, and mixtures thereof, to be combined with the core of the pharmaceutical mixture. Examples of lubricants include, but are not limited to, talc, calcium stearate, magnesium stearate, solid polyethylene glycols, sodium lauryl sulfate, inert silicon glass materials, colloidal silicon dioxide, and higher fatty acids and their alkali-metal and alkaline-earth-metal salts. In addition, various excipients such as diluents, lubricants, dyes, etc., which are disclosed in Remington's Pharmaceutical Sciences, 1995 Edition, may be used to optimize the pharmaceutical composition of the invention. The amount of the lubricants and anti-sticking agents generally varies from about 0.5% to about 20% by weight of the pharmaceutical composition, such as from about 2.5% to about 10%. Examples that can be blended herein with the core of the pharmaceutical composition include magnesium stearate, silicon dioxide and talc to a final concentration of from about 1.0% to about 7.0% by weight.

The core of the pharmaceutical mixture can be prepared in a form of granules, particles, beads, spherical beads, pellets, coated beads, coated pellets, coated particles, and other pharmaceutically acceptable shapes and sizes. This can be done by various granulation methods and other methods, such as wet and dry granulations. Wet granulation is prepared by mixing required components with various conventional well-known solvents to form granules. Alternatively, dry granulation techniques may be used to prepare the pharmaceutical composition. The mixture of the core of the pharmaceutical composition can then be incorporated into solid dosage forms, such as tablets and others, and an optional external coating is applied. For making compressed tablets, a conventional tabletting machine may be used to compress a granulated mixture of the components of the present invention into a tablet. In an alternative embodiment, the invention provides a method for preparing an extended release formulation by preparing a pharmaceutical mixture into a core and coating the core with a pharmaceutically acceptable coating material. The coated core is then incorporated into solid dosage forms.

The pharmaceutically acceptable coating material includes, but is not limited to, a rapid-disintegrating coating material, a colorant, an enteric polymer, a plasticizer, a water-soluble polymer, a water-insoluble polymer, a dye, a pigment, other disintegrants, and combinations thereof. One common example of rapid-disintegrating coating material is OPADRY, available from Colorcon, Inc. Generally enteric polymers rapidly disintegrate or dissolve at pH 5 or above. Examples of enteric polymers include methacylic acid copolymers (e.g., Eudragit™ S and Eudragit™ L, available from Rohm America, LLC), hydroxypropyl methylcellulose phthalate, hydroxypropyl methylcellulose acetate, hydroxypropyl methylcellulose succinate, carboxymethylethylcellulose, cellulose acetophthalate. In addition, examples of plasticizers include polyethylene glycol (PEG), propylene glycol, and others. Further, water-soluble polymers generally have a high degree of swelling in contact with water or aqueous media such as the stomach contents. Examples of water-soluble polymers include hydroxypropyl methylcellulose, hydroxypropyl cellulose, polyethylene oxide, and others.

Generally, the amount of the pharmaceutically acceptable coating material surrounding the core is from about 1% to about 5%, such as about 0.5% to about 2% by weight, based on the total weight of the pharmaceutical composition. It is found that the release rate of the therapeutically active agent can be controlled not only by incorporating suitable pharmaceutically acceptable polymer and pharmaceutically acceptable acid therein, but also by the thickness of the pharmaceutically acceptable coating material applied.

In yet another embodiment, a method of administering an extended release pharmaceutical composition is provided. The method includes administering the pharmaceutical composition of the invention having a therapeutically active agent in an effective amount to treat a mammal. For example, an extended release antibiotic formulation can be used in an effective amount of 500 mg per day for the treatment of bacterial infection.

EXAMPLES

Exemplary antibiotic controlled release dosage formulations are prepared and described herein. Pharmaceutical compositions having from about 40% to about 80% an antibiotic, from about 0.1% to about 30% of a pharmaceutically acceptable acid, and from about 0.1% to about 4.9% a pharmaceutically acceptable carrier base, such as high molecular weight hydroxypropyl methylcellulose, polyvinylpyrrolidone, and mixtures thereof, are formulated and tested herein. Generally, oral dosage formulations of erythromycin derivatives, such as 6-O-methoxyerythromycin A (clarithromycin), in the form of an extended release tablet are tested in vitro for their release profile and in some cases compared in vivo to healthy human subjects with a reference formulation. The reference formulation used is the commercially available Biaxin® XL Filmtab® tablet (Abbott Laboratories).

Example 1

Granulation: Clarithromycin 500 mg extended release tablets are prepared by dry granulation. Each tablet includes about 500 mg of micronized clarithromycin, about 3% to about 4.5% by weight of hydroxypropyl methylcellulose, about 10% to about 50% by weight of lactose, about 0.5% to about 3% by weight of colloidal silicon dioxide, about 0.1% to about 10% by weight of citric acid (USP grade), about 1% to about 3% by weight of talc, and about 0.5% to about 3% by weight of magnesium stearate. The tablets are prepared by passing a mixture of hydroxypropyl methylcellulose, lactose, colloidal silicon dioxide, citric acid, and talc through a 20 mesh screen and adding into a mixer to mix for approximately 10 minutes. The resulting powder mixture is then passed through a 16 mesh screen concurrently with clarithromycin and mixed for about 10 minutes. After the mixing and blending, the blend/mixture is compressed into slugs (weighed 1 g, ¾" in diameter). The slugs are then passed through a Fitzmil (available from available from The W. J. Fitzpatrick Company, Chicago, USA) equipped with a 25 mesh screen to form granules.

Tabletting: The granules are mixed with magnesium stearate for approximately two minutes and then compressed into tablets using a rotary press fitted with oval shaped punches.

Color coating: The compressed tablet is coated with OPADRY WHITE (available from Colorcon, Inc.) by first dispersing the OPADRY WHITE in purified water then applying the solution to the compressed tablet using a pan coater. The compressed tablet is coated with the coating dispersion until a theoretical coating level of approximately 1% is obtained.

Release: The resulting tablets together with reference formulation are tested in acetate buffer (pH 5) according to the procedure described in United States Pharmacopeia, Apparatus 2, at a speed of about 50 rpm, with n=3 and found to have the following release profile:

| Time (hours) | Reference % Released | Example 1 % Released |
| --- | --- | --- |
| 2 | 18 | 19 |
| 4 | 41 | 37 |
| 8 | 76 | 76 |
| 12 | 91 | 98 |

The results demonstrate a zero order release of clarithromycin prepared by the method and formulation of example 1 and a graph of the in vitro release profile is plotted in FIG. 1. As show in FIG. 1, the drug, clarithromycin is dissolved over a period of a time up to 8 hours in a linear zero order profile, using the percentage of the drug dissolved in the Y-axis and time in hours in the X-axis.

Example 2

Granulation: Clarithromycin 500 mg extended release tablets are prepared by wet granulation. Each tablet include about 500 mg of micronized clarithromycin, about 0.1% to about 4.5% by weight of hydroxypropyl methylcellulose, about 30% to about 40% by weight of lactose, about 0.5% to about 3% by weight of colloidal silicon dioxide, about 0.5% to about 5% by weight of citric acid (USP grade), about 1% to about 3% by weight of talc, and about 0.5% to about 3% by weight of magnesium stearate. The tablets are prepared by adding a mixture of clarithromycin, hydroxypropyl methylcellulose, lactose, and citric acid to a mixer and mixing for about 5 minutes. The resulting powder mixture is mixed with purified water in a granulator and mixed until granules are formed.

Tabletting: The granules are dried for approximately 16 hours at 50° C. The dried granules are passed through a Fitzmil equipped with a 30 mesh screen and mixed with colloidal silicon dioxide, magnesium stearate, and talc separately, and then compressed into tablets using a rotary press fitted with oval shaped punches.

Color coating: The compressed tablet is coated with OPADRY WHITE by first dispersing the OPADRY WHITE in purified water then applying the solution to the compressed tablet using a pan coater. The compressed tablet is coated with the coating dispersion until a theoretical coating level of approximately 1% is obtained.

Release: The resulting tablets together with reference formulation are tested in acetate buffer (pH 5) according to the procedure described in United States Pharmacopeia, Apparatus 2, at a speed of about 50 rpm, with n=3 and found to have the following release profile:

| Time (hours) | Reference % Released | Example 2 % Released |
|---|---|---|
| 2 | 18 | 15 |
| 4 | 41 | 35 |
| 8 | 71 | 69 |
| 12 | 89 | 81 |

The results demonstrate a zero order release of clarithromycin prepared by the method and formulation of example 2.

Example 3

Granulation: Clarithromycin 500 mg extended release tablets are prepared by wet granulation. Each tablet includes about 500 mg of micronized clarithromycin (USP grade), about 0.1% to about 0.9% by weight of polyvinylpyrrolidone, about 3% to about 4% by weight of hydroxypropyl methylcellulose, about 30% to about 45% by weight of anhydrous lactose, about 0.1% to about 5% by weight of colloidal silicon dioxide, about 0.5% to about 4.5% by weight of citric acid (USP grade), about 0.5% to about 5% by weight of talc, and about 0.1% to about 5% by weight of magnesium stearate. The tablets are prepared by passing a mixture of polyvinylpyrrolidone, half of the anhydrous lactose needed, and citric acid through a 25 mesh screen and adding the mixture into a granulator. Clarithromycin and the other half of the anhydrous lactose are added into the granulator to be mixed for about 10 minutes. The resulting blend/mixture is mixed with purified water, the granulating liquid, inside the granulator and mixed until granules are formed.

Tabletting: The granules are dried at 50° C. overnight. The dried granules are passed through a Comil (available from Quadro Company, Ontario, Canada) equipped with a #813 mesh screen. The screened granules are mixed with talc, colloidal silicon dioxide, hydroxypropyl methylcellulose and magnesium stearate for approximately 12 minutes totally and then compressed into tablets using a rotary press fitted with oval shaped punches.

Enteric coating: The compressed tablet is coated with Eudragit L30 D-55 (available from Rohm America, LLC) and propylene glycol by first mixing Eudragit L30 D-55 and propylene glycol in purified water and then applying the resulting solution to the compressed tablet using a pan coater. The compressed tablet is coated with the coating material until a theoretical coating level of approximately 1% is obtained.

Release: The resulting tablets together with reference formulation are tested in phosphate buffer (pH 5) according to the procedure described in United States Pharmacopeia, Apparatus 2, at a speed of about 50 rpm, with n=3 and found to have the following release profile:

| Time (hours) | Reference % Released | Example 3 % Released |
|---|---|---|
| 2 | 21 | 22 |
| 6 | 58 | 68 |
| 12 | 90 | 100 |

The results demonstrate a zero order release of clarithromycin prepared by the method and formulation of example 3.

Example 4

Granulation: Clarithromycin 500 mg extended release tablets are prepared by wet granulation. Each tablet include about 500 mg of micronized clarithromycin (USP grade), about 2% to about 4.5% by weight of hydroxypropyl methylcellulose, about 20% to about 40% by weight of anhydrous lactose, about 0.1% to about 2% by weight of polysorbate 80, about 0.1% to about 5% by weight of colloidal silicon dioxide, about 0.5% to about 5% by weight of citric acid (USP grade), about 0.5% to about 5% by weight of talc, and about 0.1% to about 4% by weight of magnesium stearate. The tablets are prepared by passing a mixture of hydroxypropyl methylcellulose, half of the anhydrous lactose needed, citric acid through a 25 mesh screen and adding into a granulator. Clarithromycin and the other half of the anhydrous lactose are added into the granulator to be mixed for about 10 minutes. The resulting blend/mixture is mixed with an aqueous solution of polysorbate 80 inside the granulator and blended until granules are formed.

Tabletting: The granules are dried at 50° C. overnight. The dried granules are passed through a Comil equipped with a #813 mesh screen. The screened granules are mixed with screened talc, colloidal silicon dioxide, and magnesium stearate for approximately 12 minutes total and then compressed into tablets using a rotary press fitted with oval shaped punches.

Enteric coating: The compressed tablet is coated with a solution of Eudragit L30 D-55 (available from Rohm America, LLC), sodium chloride, and propylene glycol in purified water. The resulting solution is applied to the compressed tablet using a pan coater. The compressed tablet is coated with the coating solution until a theoretical coating level of approximately 1% is obtained.

Release: The resulting tablets together with reference formulation are tested in phosphate buffer (pH 5) according to the procedure described in United States Pharmacopeia, Apparatus 2, at a speed of about 50 rpm, with n=3 and found to have the following release profile:

| Time (hours) | Reference % Released | Example 4 % Released |
|---|---|---|
| 2 | 15 | 15 |
| 6 | 48 | 46 |
| 12 | 79 | 82 |
| 20 | 100 | 94 |
| 24 | 100 | 94 |

The resulting tablets are also tested in phosphate buffer (pH 6.8) according to the procedure described in United States Pharmacopeia, Apparatus 2, at a speed of about 50 rpm, with n=3 and found to have the following release profile:

| Time (hours) | Reference % Released | Example 4 % Released |
|---|---|---|
| 2 | 11 | 7 |
| 6 | 32 | 28 |

-continued

| Time (hours) | Reference % Released | Example 4 % Released |
|---|---|---|
| 12 | 57 | 53 |
| 20 | 67 | 77 |
| 24 | 69 | 76 |

The results demonstrate a zero order release of clarithromycin prepared by the method and formulation of example 4.

Example 5

Clarithromycin 500 mg extended release tablets are prepared according to embodiments of the invention. The extended release tablets of the invention are tested together with reference formulation in a 2-way crossover pilot food-effect bioavailability study. The average absorption profile in six healthy subjects as compared to the reference is as follows:

|  | Geomean |
|---|---|
| $C_{max}$ Ratio | 0.946 |
| AUC Ratio | 0.899 |

Note: AUC means the area under a curve which plots the serum concentration (e.g., in μg/mL) of clarithromycin in the Y-axis against time as the X-axis and $C_{max}$ means the maximum serum concentration under such a curve.

While the foregoing is directed to embodiments of the present invention, other and further embodiments of the invention may be devised without departing from the basic scope thereof, and the scope thereof is determined by the claims that follow.

What is claimed is:

1. A pharmaceutical composition, comprising:
a therapeutically active agent;
from about 0.1% to about 4.9% by weight of a swellable and water-soluble pharmaceutically acceptable polymer; and
from about 0.1% to about 30% by weight of a pharmaceutically acceptable acid, wherein the pharmaceutical composition has a zero order release profile of the therapeutically active agent.

2. The pharmaceutical composition of claim 1, wherein the therapeutically active agent is selected from the group consisting of antibiotics, erythromycin, clarithromycin, azithromycin, amoxicillin, tetracycline, anti-hypertensives, calcium channel blockers, β-blockers, analgesics, anti-neoplastic agents, anti-malarials, non-steroidal anti-inflammatory drugs (NSAID), diuretics, anti-arrythmia agents and combinations thereof.

3. The pharmaceutical composition of claim 1, wherein the pharmaceutical composition comprises from about 10% to about 95% by weight of the therapeutically active agent.

4. The pharmaceutical composition of claim 1, wherein the pharmaceutically acceptable polymer is selected from the group consisting of hydrophilic polymer, polyvinylpyrrolidone, hydroxypropyl cellulose, hydroxypropyl methylcellulose, methyl cellulose, polyethylene oxide, maltodextrin, natural gum, and and combinations thereof.

5. The pharmaceutical composition of claim 1, wherein the pharmaceutically acceptable polymer is hydroxypropyl methylcellulose of high viscosity grade with viscosity greater than about 5,000 cps.

6. The pharmaceutical composition of claim 1, wherein the pharmaceutically acceptable polymer is polyvinylpyrrolidone of high viscosity grade with viscosity at least about 55 cps.

7. The pharmaceutical composition of claim 4, wherein the pharmaceutically acceptable polymer is a mixture of hydroxypropyl methylcellulose and polyvinylpyrrolidone.

8. The pharmaceutical composition of claim 1, wherein the composition comprises from about 0.1% to about 4.5% by weight of hydroxypropyl methylcellulose.

9. The pharmaceutical composition of claim 1, wherein the pharmaceutically acceptable acid is selected from the group consisting of organic acids, carboxylic acids, keto acids, α-hydroxy acids, β-hydroxy acids, and combinations thereof.

10. The pharmaceutical composition of claim 1, further comprising one or more pharmaceutically acceptable excipients selected from the group consisting of fillers, extenders, binders, blending agents, surfactants, emulsifiers, dispersing agents, defoamers, lubricants, nonstick agents, blenders, coating materials, glidants, anti-sticking agents, diluents, dyes, pigments, dispersants, wetting agents, and combinations thereof.

11. The pharmaceutical composition of claim 1, wherein the pharmaceutical composition comprises from about 30% to about 80% by weight of an erythromycin derivative, from about 1.5% to about 4.5% by weight of hydroxypropyl methylcellulose, and from about 0.1% to about 10% by weight of a carboxylic acid.

12. The pharmaceutical composition of claim 1, wherein the pharmaceutical composition comprises from about 30% to about 80% by weight of clarithromycin, from about 1.5% to about 4.5% by weight of hydroxypropyl methylcellulose, from about 0.1% to about 10% by weight of citric acid, and from about 10% to about 50% by weight of lactose.

13. An extended release pharmaceutical composition, comprising:
a core of a pharmaceutical mixture; and
a coating layer of a pharmaceutically acceptable coating material, wherein the pharmaceutical mixture comprises:
a therapeutically active agent;
from about 0.1% to about 4.9% by weight of a swellable and water-soluble pharmaceutically acceptable polymer; and
from about 0.1% to about 30% by weight of a pharmaceutically acceptable acid, such that the release profile of the therapeutically active agent is at a zero order release rate.

14. The pharmaceutical composition of claim 13, wherein the therapeutically active agent is from about 10% to about 95% of the total weight of the extended release pharmaceutical composition and is selected from the group consisting of antibiotics, erythromycin, clarithromycin, azithromycin, amoxicillin, tetracycline, anti-hypertensives, calcium channel blockers, β-blockers, analgesics, anti-neoplastic agents, anti-malarials, non-steroidal anti-inflammatory drugs (NSAID), diuretics, anti-arrythmia agents and combinations thereof.

15. The extended release pharmaceutical composition of claim 13, wherein the pharmaceutical mixture further comprises one or more pharmaceutically acceptable excipients selected from the group consisting of fillers, extenders, binders, blending agents, surfactants, emulsifiers, dispersing agents, defoamers, lubricants, nonstick agents, blenders, coating materials, glidants, anti-sticking agents, diluents, dyes, pigments, dispersants, wetting agents, and combinations thereof.

16. The extended release pharmaceutical composition of claim 13, wherein the pharmaceutically acceptable coating material is selected from the group consisting of dye, pigment, colorant, enteric polymer, plasticizer, rapid-disintegranting coating material, methacrylate copolymer, hydroxypropyl methylcellulose phthalate, hydroxypropyl methylcellulose acetate, hydroxypropyl methylcellulose succinate, carboxymethylethylcellulose, cellulose acetophthalate, disintegrant, polyethylene glycol, propylene glycol, and combinations thereof.

17. The extended release pharmaceutical composition of claim 13, wherein the pharmaceutically acceptable coating material is provided for rapid disintegration of the therapeutically active agent at pH 5 or above.

18. The extended release pharmaceutical composition of claim 13, wherein the pharmaceutically acceptable polymer is selected from the group consisting of hydrophilic polymer, polyvinylpyrrolidone, hydroxypropyl cellulose, hydroxypropyl methylcellulose, methyl cellulose, polyethylene oxide, maltodextrin, natural gum, and and combinations thereof.

19. The extended release pharmaceutical composition of claim 13, wherein the pharmaceutically acceptable acid is selected from the group consisting of organic acids, carboxylic acids, keto acids, α-hydroxy acids, β-hydroxy acids, and combinations thereof.

20. The extended release pharmaceutical composition of claim 13, wherein the pharmaceutical mixture is prepared into a form selected the group consisting of granules, spherical beads, tablets, pellets, particles, coated beads, coated pellets, coated particles, and combinations and mixtures thereof.

21. An extended release pharmaceutical composition, comprising:
a core of a pharmaceutical mixture having from about 10% to about 95% of an antibiotic, from about 0.1% to about 4.9% by weight of a swellable and water-soluble pharmaceutically acceptable polymer, and from about 0.1% to about 30% by weight of a pharmaceutically acceptable acid; and
a coating layer of a pharmaceutically acceptable coating material, such that the release profile of the antibiotic is at a zero order release rate.

22. The extended release pharmaceutical composition of claim 21, wherein the pharmaceutical mixture comprises from about 30% to about 80% by weight of clarithromycin, from about 1.5% to about 4.5% by weight of hydroxypropyl methylcellulose, from about 0.1% to about 30% by weight of citric acid, and from about 10% to about 50% by weight of lactose.

23. The extended release pharmaceutical composition of claim 21, wherein the pharmaceutical mixture is compressed into granules.

24. The extended release pharmaceutical composition of claim 21, wherein the pharmaceutically acceptable coating material is Eudragit.

25. A method of preparing a pharmaceutical composition, comprising:
forming a core having a pharmaceutical mixture; and
coating the core with a coating layer of a pharmaceutically acceptable coating material, wherein the pharmaceutical mixture comprises:
a therapeutically active agent;
from about 0.1% to about 4.9% by weight of a swellable and water-soluble pharmaceutically acceptable polymer; and
from about 0.1% to about 30% by weight of a pharmaceutically acceptable acid.

26. The method of claim 25, further comprising compressing the pharmaceutical composition into a dosage form selected from the group consisting of an oral dosage form, a solid dosage form, and combinations thereof.

27. The method of claim 25, wherein the core is formed by mixing the pharmaceutical mixture and compressing the mixture into a tablet.

28. The method of claim 25, wherein the core is formed by a technique selected from the group consisting of dry granulation and wet granulation.

29. The method of claim 25, wherein the therapeutically active agent is selected from the group consisting of antibiotics, erythromycin, clarithromycin, azithromycin, amoxicillin, tetracycline, anti-hypertensives, calcium channel blockers, β-blockers, analgesics, anti-neoplastic agents, anti-malarials, non-steroidal anti-inflammatory drugs (NSAID), diuretics, anti-arrythmia agents and combinations thereof.

30. A method of administering an extended release pharmaceutical composition, comprising:
administering an anti-bacterial composition of claim 21 in an effective amount to a mammal for the treatment of bacterial infection.

* * * * *